US00PP17181P2

(12) United States Plant Patent
Jones

(10) Patent No.: US PP17,181 P2
(45) Date of Patent: Oct. 31, 2006

(54) ***DIASCIA* PLANT NAMED 'PENIMP'**

(50) Latin Name: *Diascia×hybrida*
Varietal Denomination: PENIMP

(76) Inventor: Sidney James Jones, 14 Avondale Road, Pontnewydd, Cwmbran, Wales, NP44 1UD (GB)

( * ) Notice: Subject to any disclaimer, the term of this patent is extended or adjusted under 35 U.S.C. 154(b) by 0 days.

(21) Appl. No.: 11/189,181

(22) Filed: Jul. 25, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers

(57) ABSTRACT

A new cultivar of *Diascia* plant named 'PENIMP' that is characterized by compact habit, green leaves, sterility and pink flowers that form a complete canopy of bloom by early summer. In combination these traits set 'PENIMP' apart from all other existing varieties of *Diascia* known to the inventor.

3 Drawing Sheets

Genus: *Diascia*. Species: ×*hybrida*.
Denomination: 'PENIMP'.

BACKGROUND OF THE INVENTION

The present invention relates to a new and distinct cultivar of twinspur, a perennial that is grown for use in raised beds, borders, hanging baskets, and patio containers. The new cultivar is known botanically as *Diascia* and will be referred to hereinafter by the cultivar name 'PENIMP'.

The inventor has been interested and has collected plants of the genus *Diascia* since the early 1990s. *Diascia,* which is native to southern Africa, provides showy annual and perennial (in mild climates) plants whose predominant flower color range in nature is in the range of soft to dark pink, also white, lavender-pink, salmon and apricot. Plants of *Diascia* which are raised from seed are inherently variable in growth habit, ranging from loose, weak plants with brittle stems to plants with significantly shorter internodes resulting in more compact forms and therefore more dense flowering characteristics. Various breeding programs, including the inventor's, have aimed to develop improvements in plant habit and also an extension in the color range into deep pink or red or orange shades and ideally with very similar compact habits for each color.

In 1995, the inventor commenced a deliberate program to develop a range of *Diascias* whose characteristics would be common throughout, namely an extremely compact plant habit with bright flower colors, and in a range of colors. In 1995 the inventor selected from his collection several plants with the dwarfest habit and hand-pollinated amongst them. The plants involved in the hybridization are unknown although some were numbered selections from prior work.

The seedlings raised during 1995 flowered in the same year and many were retained for further observation in 1996 and 1997. In May 1997, the inventor determined that one plant, PENDAN (unpatented), exhibited exceptional characteristics of dense habit and bright clear saturated pink flowers.

The new *Diascia,* PENIMP was selected in 2002 as a single plant within a crop of trial plants which had all been grown from *in vitro* cuttings of PENDAN which had been chemically treated by the inventor. These *in vitro* cuttings were taken from the inventor's laboratory stock of virus-free plants of PENDAN. PENIMP is a chemically induced mutation of PENDAN and was selected by the inventor for its outstanding floriferousness which causes a plant of PENIMP to be completely covered in flowers with no foliage visible. The inventor considers that this ability to form a dense canopy of flower sets PENIMP apart from other *Diascias* known to the inventor, including PENDAN which exhibits similar plant habit and identical flower color, but a lesser density of flowers. The inventor has not observed any seed formation on PENIMP.

The parent of 'PENIMP' is an individual whole plant of *Diascia* 'PENDAN'. 'PENIMP' is distinguishable from the parent by sterility, and profuse blooming. The closest comparison plant known to the inventor is *Diascia* 'PENDER', which is also derived from 'PENDAN'. 'PENDER' is the subject of a separate application for grant of a U.S. Plant Patent. 'PENDER' and 'PENIMP' exhibit similar plant habit characteristics. 'PENDER' produces deep salmon-pink flowers whereas 'PENIMP' produce mid-pink flowers. 'PENDER' is very floriferous whereas 'PENIMP' is exceptionally floriferous.

The first asexual propagation of the new *Diascia* cultivar 'PENIMP' was conducted in 2002 by the inventor at his nursery in Newport, Gwent, England. The method of asexual propagation used was vegetative tip cuttings. Since that time the unique and distinguishing characteristics of 'PENIMP' have been determined stable, fixed, and reproduce true to type in successive generations of asexual reproduction.

SUMMARY OF THE INVENTION

The following traits have been repeatedly observed and represent the characteristics of the new *Diascia* cultivar 'PENIMP'. These traits in combination distinguish 'PENIMP' from all other commercial varieties of *Diascia* known to the inventor. 'PENIMP' has not been tested under all possible conditions and phenotypic differences may be observed with variations in environmental, climatic, and cultural conditions, without however, any difference in genotype.

1. 'PENIMP' exhibits compact habit.
2. 'PENIMP' exhibits pink flowers.
3. 'PENIMP' blooms profusely spring through fall.
4. 'PENIMP' does not set seed.
5. 'PENIMP' exhibits green leaves.
6. 'PENIMP' is propagated using the method of vegetative tip cuttings.
7. 'PENIMP' is 25 cm. in height and 50 cm. in width in a 5-liter container after one season.
8. The cultural requirements of 'PENIMP' are well-draining soil, full sun, and regular water.
9. 'PENIMP' is suitable for use in raised beds, borders, hanging baskets, and patio containers.
10. 'PENIMP' is hardy to USDA Zone 7.

BRIEF DESCRIPTION OF THE DRAWINGS

The accompanying color drawings

Figure 1:
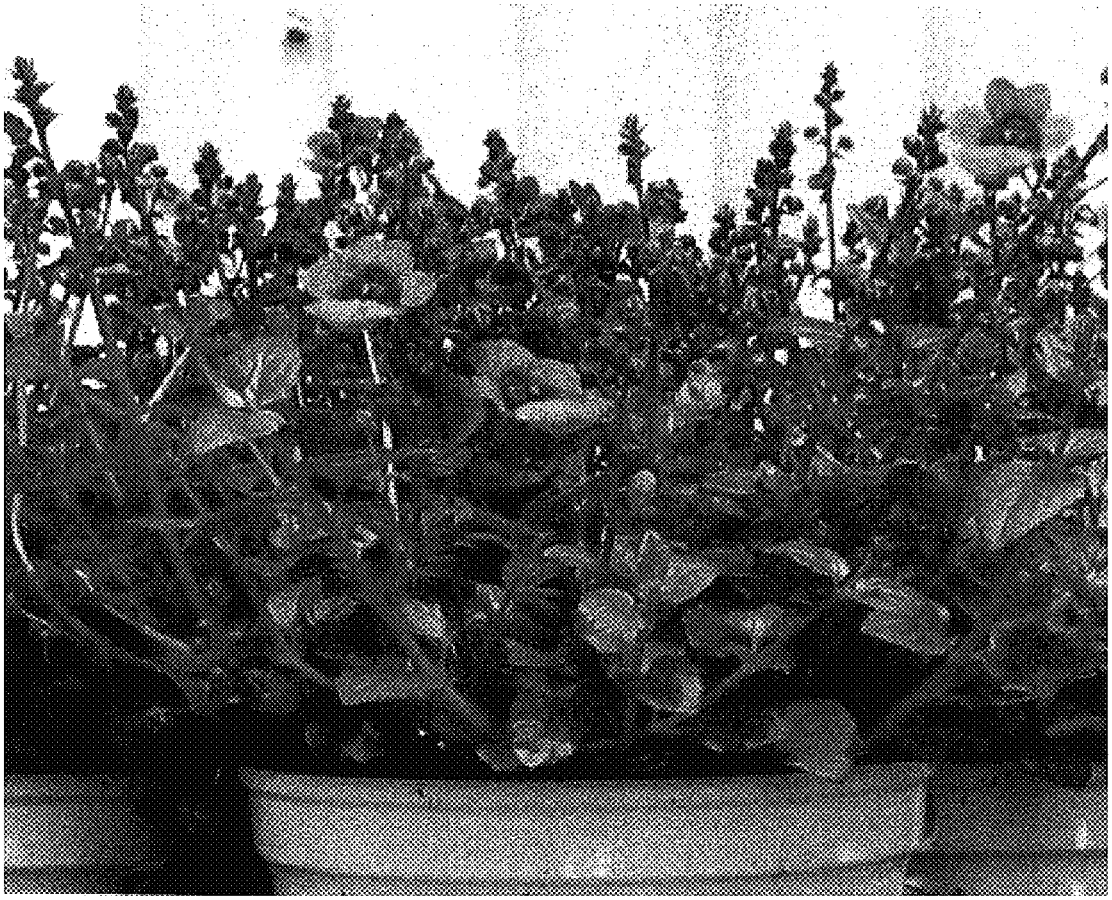
FIG. 1, FIG. 2 and FIG. 3 illustrate the overall appearance of the new *Diascia* cultivar 'PENIMP' showing the colors as true as it is reasonably possible to obtain in colored reproductions of this type. Colors in the drawings may differ from the color values cited in the detailed botanical description, which accurately describes the actual colors of the new variety of *Diascia* named 'PENIMP'.

The drawing labeled as FIG. 1 depicts one whole plant of 'PENIMP' which has been grown to bud and first flower in a 4 inch diameter container out of doors in Arroyo Grande, Calif. The illustrated plant is approximately 15 weeks old from a cutting.

Figure 2:
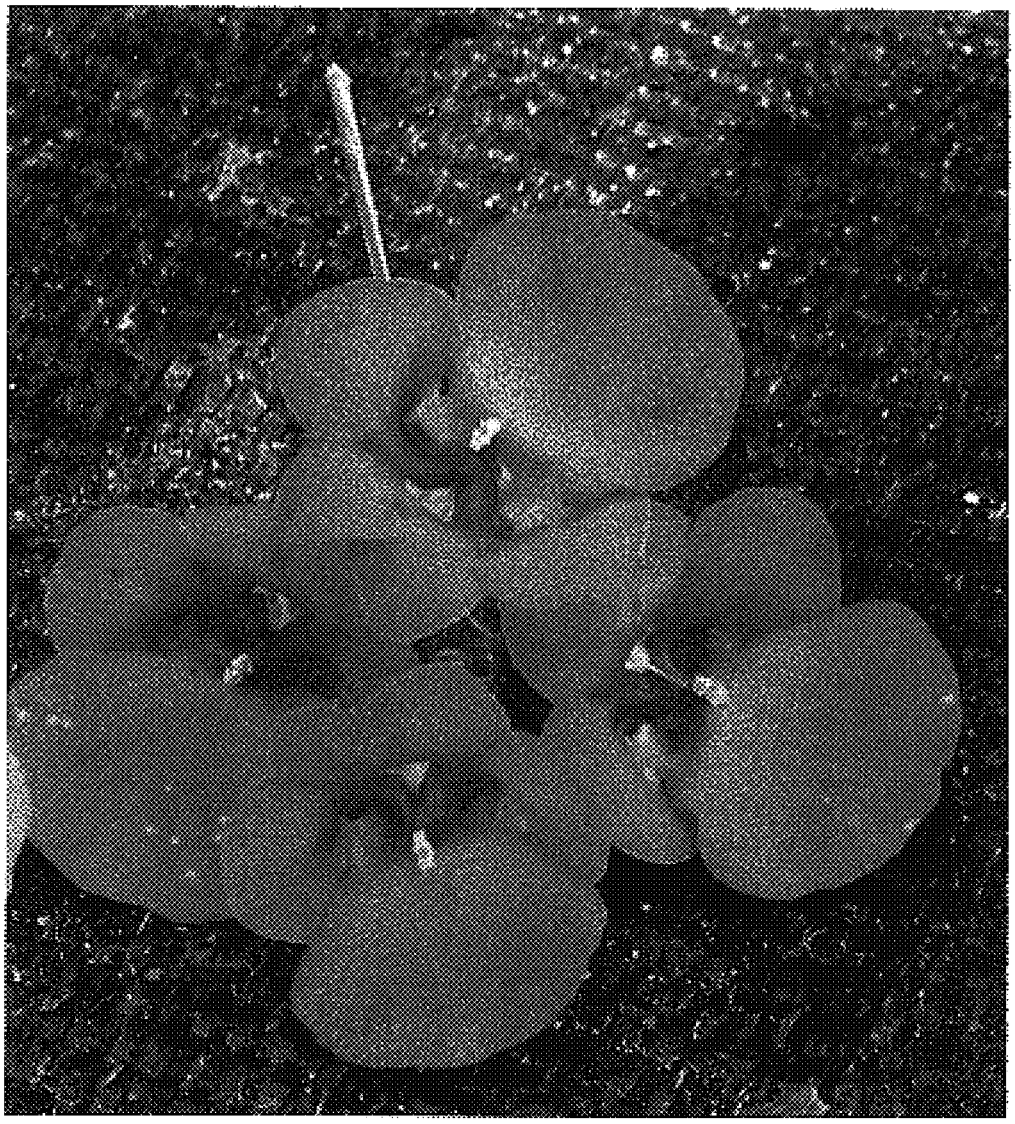

The drawing labeled as FIG. 2 illustrates a single inflorescence of 'PENIMP' with four individual flowers.

Figure 3:
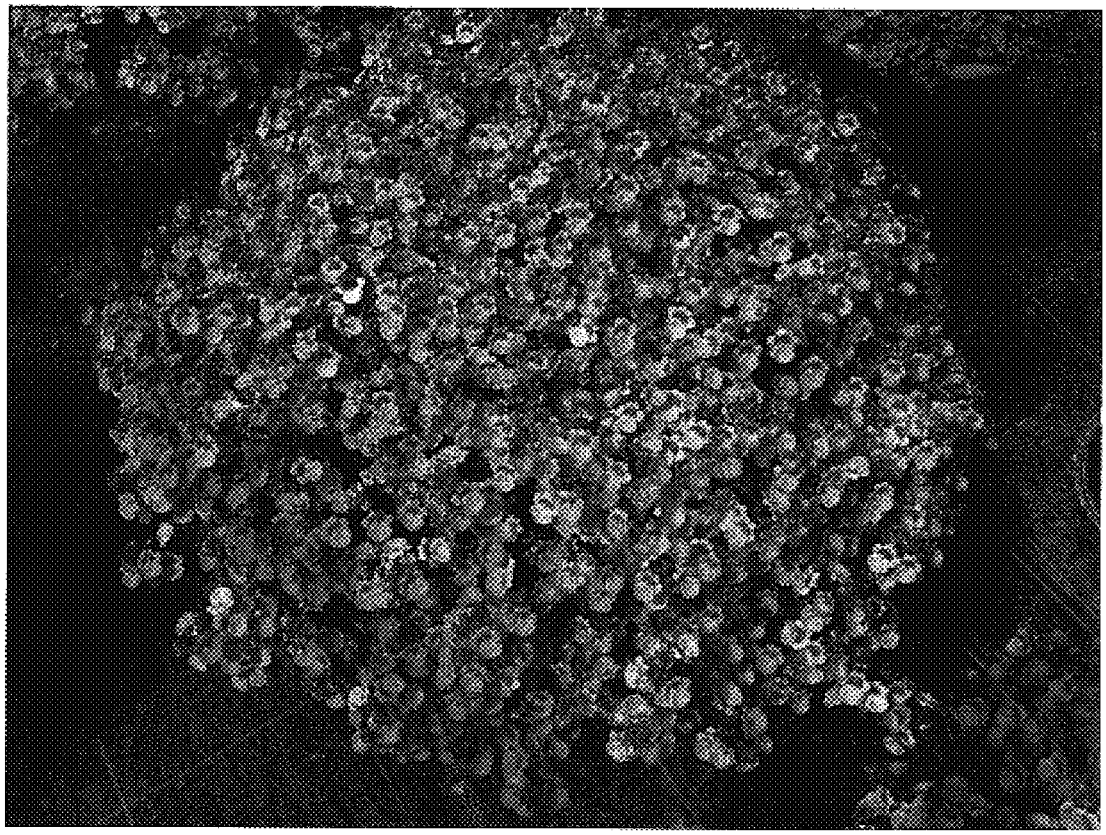

The drawing labeled as FIG. 3 depicts a single plant of 'PENIMP' which has been grown in the inventor's greenhouse in Newport, Wales, United Kingdom. The drawing illustrates the complete flower canopy which is typical of a plant of 'PENIMP' in early summer. The illustrated plant was started as a cutting in the previous fall, potted into a four inch container and over-wintered in a frost-protected greenhouse, and then pinched and potted into a 5 liter container in spring and allowed to grow on to full flower by early summer as shown.

All the drawings have been made using conventional photographic techniques and although colors may appear different from actual colors due to light reflectance, they are as accurate as possible by conventional photography.

BOTANICAL DESCRIPTION OF THE PLANT

The following is a detailed description of the new *Diascia* cultivar 'PENIMP'. Data was collected June 2005 in Arroyo Grande, Calif. from 18 month old plants in 5-liter containers. The color determinations are in accordance with the 2001 edition of The Royal Horticultural Society Colour Chart, except where general color terms of ordinary dictionary significance are used. The new *Diascia* variety named 'PENIMP' has not been observed under all possible environmental conditions. Phenotypic differences may be observed with variations in environmental, climatic, and cultural conditions, without however, any difference in genotype.

Botanical classification: *Diascia×hybrida* 'PENIMP'.
Genus: *Diascia.*
Species: *×hybrida.*
Denomination: 'PENIMP'.
Common name: Twinspur.
Commercial classification: Perennial.
Plant uses: Suitable for use in raised beds, borders, hanging baskets and patio containers.
Cultural requirements: Provide well-draining soil, full sun and regular water.
Hardiness: Hardy to USDA Zone 7.
Parentage: *Diascia* 'PENIMP' originated as a chemically induced mutation of the following parent:
*Parent plant.*—An individual whole plant of *Diascia* 'PENDAN'.
Plant description:
*Blooming seasons.*—Spring, summer and fall.
*Plant habit.*—Compact habit.
*Plant form.*—Mounding form.
*Plant vigor.*—Vigorous.
*Plant propagation method.*—Propagated using the method of vegetative tip cuttings.
*Plant height.*—Plant is 25 cm. in height in a 5-liter container.
*Plant width.*—Plant is 50 cm. in width in a 5-liter container.
*Number of flowers and buds per inflorescence.*—An average of 10–15 flowers and 10–15 buds are present on an individual inflorescence.
*Root system.*—Fine and fibrous roots.
*Resistance and susceptibility to diseases and pests.*—No resistance or susceptibility to pests or disease is known to the inventor.
*Crop time.*—3 months are needed to produce a finished 1-liter commercial container from a rooted cutting.
*Time to develop roots.*—10–14 days are needed to develop roots on an initial cutting.
*Special considerations.*—Encourage new branching by periodic pruning.
Stem, branches: The stem produces 3–4 branching stems at 1 cm. above the surface. Each branching stem produces 1–2 nodal sub-branches. Each sub-branch produces further nodal branching stems which flower at approximately 2 weeks after final pinch.
*Flowering stems per plant.*—Approximately 100.
*Stem shape.*—Stem is quadrilateral in shape.
*Stem color.*—Stem is 138B in color.
*Stem length.*—Stem is 1 cm in length.
*Stem diameter.*—Stem is 4 mm. in diameter.
*Internode length.*—Internode ranges from 2 cm. to 4.50 cm. in length.
*Stem surface*—Glabrous stem surface.
*Branching stem length at flowering.*—19 to 25 cm.
*Branching stem diameter.*—2 mm.
Foliage:
*Average number of leaves per branching stem.*—4–8.
*Leaf arrangment.*—Opposite.
*Leaf division.*—Simple.
*Leaf shape.*—Leaf is cordate in shape.
*Leaf base.*—Cordate base.
*Leaf apex.*—Acute apex.
*Leaf margin.*—Denticulate margin.
*Leaf venation pattern.*—Pinnate vein pattern.

*Vein color* (*abaxial surfaces*).—Vein is 138B in color.
*Vein color* (*adaxial surfaces*).—Vein is 137A in color.
*Leaf surface* (*abaxial surface*).—Glabrous leaf surface.
*Leaf surface* (*adaxial surface*).—Glabrous leaf surface.
*Leaf color* (*abaxial surface*).—Leaf is 138B in color.
*Leaf color* (*adaxial surface*).—Leaf is 137A in color.
*Leaf appearance* (*abaxial surface*).—Matte in appearance.
*Leaf appearance* (*adaxial surface*).—Semi-gloss in appearance.
*Leaf length.*—Leaves on an individual plant range from 1.25 cm. to 2.50 cm. in length.
*Leaf width.*—Leaves on an individual plant range from 1 cm. to 2 cm. in width.
*Leaf attachment.*—Petiolate.
*Petiole surface.*—Stipitate glandular petiole surface.
*Petiole dimensions.*—Petiole dimensions are 5 mm. in length and 2 mm. in diameter.
*Petiole shape.*—Sulcate in shape.
*Petiole color.*—Petiole is 138B in color.
*Leaf fragrance.*—No leaf fragrance is observed.

Flower:
*Inflorescence type.*—Terminal raceme.
*Inflorescence dimensions.*—4 cm. in depth and 5 cm. in diameter.
*Flower aspect.*—Flowers on an individual plant are a combination of outward and upward aspect.
*Flowers persistent or self-cleaning.*—Persistent.
*Flower shape.*—Flower is calcarate in shape.
*Flower depth.*—Flower is 1 cm. in depth.
*Flower diameter.*—Flower is 1.50 cm. in diameter.
*Flower color.*—Individual colors 64B, 64C, 64D, N77A, and 5A are present on an individual flower.
*Petals.*—5 petals in number.
*Petal surface.*—Petal surface is glabrous.
*Petals fused or unfused.*—Petals are basally fused.
*Petal margin.*—Entire margin.
*Petal apex.*—Obtuse apex.
*Petal base.*—Rounded base.
*Petal shape.*—Petal shapes orbicular and reniform are individually present on an individual flower.
*Petal width.*—Petals that are 0.25 cm., 0.50 cm. and 1 cm. in width are individually present on an individual flower.
*Petal length.*—Petals that are 0.50 cm. and 0.75 cm. in length are individually present on an individual flower.
*Petal color* (*abaxial surface*).—Petal is 64D in color.
*Petal color* (*adaxial surface*).—Petal is 64C in color.
*Corolla window color.*—Corolla window is 5A in color.
*Corolla window dimensions.*—Corolla window dimensions are 2 mm. in length and 2 mm. in width.
*Calcar.*—2 in number.
*Calcar surface.*—Calcar surface is glabrous.
*Calcar dimensions.*—Calcar is 6 mm. in depth and 2 mm. in diameter.
*Calcar color.*—Individual colors 64B and N77A are present on an individual calcar.
*Bud shape.*—Bud is globose in shape.
*Bud surface.*—Bud surface is stipitate glandular.
*Bud color.*—Bud is 64B in color.
*Bud dimensions.*—Bud dimensions are 4 mm. in length and 4 mm. in width.
*Peduncle color.*—Peduncle is 178A in color.
*Peduncle dimensions.*—Peduncle dimensions are 1.50 cm. in length and 0.50 mm. in diameter.
*Peduncle shape.*—Peduncle is quadrilateral in shape.
*Peduncle surface.*—Peduncle surface is stipitate glandular.
*Pedicel color.*—Pedicel is 178A in color.
*Pedicel dimensions.*—Pedicel dimensions are 0.50 cm. in length and 0.25 mm. in width.
*Pedicel shape.*—Pedicel is cylindrical in shape.
*Pedicel surface.*—Pedicel surface is stipitate glandular.
*Calyx.*—Present.
*Calyx shape.*—Stelliform in shape.
*Calyx color.*—Calyx is 138A in color.
*Number of sepals.*—Five sepals in number.
*Sepals fused or unfused.*—Sepals are unfused.
*Sepal color* (*adaxial and abaxial surfaces*).—Sepal is 138A in color.
*Sepal surface.*—Sepal surface is stipitate glandular.
*Sepal shape.*—Sepal is closest to oblanceolate in shape.
*Sepal dimensions.*—Sepal dimensions are 4 mm. in length and 0.75 mm. in width.
*Sepal apex.*—Acute apex.
*Sepal base.*—Truncate base.
*Sepal margin.*—Entire margin.
*Blooming months.*—Flowers bloom April through November.
*Lastingness of flower on the plant.*—An individual flower lasts from 5 to 10 days.
*Flower fragrance.*—No fragrance is observed.

Reproductive organs:
*Stamens.*—4 stamens in number.
*Stamen color.*—Stamens are 59A in color.
*Stamen surface.*—Stamen surface is stipitate glandular.
*Stamen dimensions.*—Stamen dimensions are 4 mm. in length and 0.50 mm. in width.
*Anther dimensions.*—Anther dimensions are 2 mm. in length and 1 mm. in diameter.
*Anther shape.*—Globose in shape.
*Anther color.*—Anther is 5A in color.
*Quantity of pollen.*—Large amount of pollen observed.
*Color of pollen.*—Pollen is 5A in color.
*Pistil.*—One pistil in number.
*Pistil color.*—Pistil is 145A in color.
*Pistil surface.*—Pistil surface is stipitate glandular.
*Pistil dimensions.*—Pistil dimensions are 5 mm. in length and 0.50 mm. in width.
*Ovary position.*—Ovary is in superior position.
*Ovary color.*—Ovary is 145A in color.
*Ovary shape.*—Ovary is globose in shape.
*Ovary dimensions.*—Ovary dimensions are 2 mm. in height and 2 mm. in width.

Seed: 'PENIMP' is sterile and does not produce seed.

It is claimed:

1. A new and distinct cultivar of *Diascia* plant named 'PENIMP' as described and illustrated herein.

* * * * *